(12) United States Patent
Dicke et al.

(10) Patent No.: US 8,871,842 B2
(45) Date of Patent: Oct. 28, 2014

(54) METHOD FOR PRODUCING A COMPOUND WITH AT LEAST ONE AT LEAST MONOSUBSTITUTED AMINO GROUP

(75) Inventors: Rene Dicke, Leonding (AT); Andreas Endesfeder, Overath (DE); Martin Burger, Traunstein (DE); Christoph Hahn, Linz (AT); Clemens Schwarzinger, Weis (AT); Wolfgang Fuerst, Leonding (AT); Harald Schmidt, Linz (AT)

(73) Assignee: Borealis Agrolinz Melamine GmbH, Linz (AT)

( * ) Notice: Subject to any disclaimer, the term of this patent is extended or adjusted under 35 U.S.C. 154(b) by 1060 days.

(21) Appl. No.: 12/934,558

(22) PCT Filed: Mar. 27, 2009

(86) PCT No.: PCT/EP2009/002430
§ 371 (c)(1),
(2), (4) Date: Feb. 1, 2011

(87) PCT Pub. No.: WO2009/121603
PCT Pub. Date: Oct. 8, 2009

(65) Prior Publication Data
US 2011/0178212 A1   Jul. 21, 2011

(30) Foreign Application Priority Data

Mar. 31, 2008   (DE) .......................... 10 2008 016 964

(51) Int. Cl.
| | | |
|---|---|---|
| C08K 5/34 | (2006.01) | |
| C07C 275/00 | (2006.01) | |
| C07D 251/18 | (2006.01) | |
| C07C 273/18 | (2006.01) | |
| C07D 251/70 | (2006.01) | |

(52) U.S. Cl.
CPC ............ *C07C 273/18* (2013.01); *C07D 251/18* (2013.01); *C07D 251/70* (2013.01)
USPC .......................................... 524/100; 564/61

(58) Field of Classification Search
CPC . C08K 5/34922; C08K 5/3492; C08K 5/3462
USPC ........ 524/100, 216; 544/196, 205; 564/61, 30
See application file for complete search history.

(56) References Cited

U.S. PATENT DOCUMENTS

| | | | |
|---|---|---|---|
| 2,385,766 A | 9/1945 | Thurston | |
| 4,668,785 A | 5/1987 | Ebel et al. | |
| 5,792,867 A * | 8/1998 | Tanaka et al. ................. | 544/196 |
| 7,405,327 B2 | 7/2008 | Haese et al. | |
| 2006/0084775 A1 | 4/2006 | Rische et al. | |
| 2006/0100317 A1 | 5/2006 | Ratzsch et al. | |

FOREIGN PATENT DOCUMENTS

| | | |
|---|---|---|
| EP | 0125616 A1 | 11/1984 |
| EP | 0166297 A1 | 1/1986 |
| EP | 0711760 A1 | 5/1996 |
| EP | 0882720 A1 | 12/1998 |
| EP | 1057821 A1 | 12/2000 |
| JP | 8092226 A | 4/1996 |
| JP | 200063369 A | 2/2000 |
| JP | 2000063360 A | 2/2000 |
| SU | 891696 A1 | 12/1981 |
| WO | 03106558 A1 | 12/2003 |
| WO | 2005110969 A1 | 11/2005 |
| WO | 2006032373 A1 | 3/2006 |

OTHER PUBLICATIONS

Magerramov et al., "Synthesis of Substituted Ureas from Urea and Halohydrins", Russian Journal of Applied Chemistry, (2004), pp. 1667-1669, vol. 77(10).
Shinoda et al., "Shape-selective N-methylation of melamine with methanol by use of Ru/mordenite catalyst in the liquid phase", Applied Catalysis A: General, (2000), pp. 375-381, 194-195.

* cited by examiner

*Primary Examiner* — Susannah Chung
*Assistant Examiner* — Atnaf Admasu
(74) *Attorney, Agent, or Firm* — The Webb Law Firm

(57) ABSTRACT

The invention relates to a method for producing at least one compound having at least one at least monosubstituted amino group. According to the invention, a starting substance having at least one amino group is reacted with an alcohol in a reaction mixture in the presence of ammonia.

24 Claims, No Drawings

US 8,871,842 B2

METHOD FOR PRODUCING A COMPOUND WITH AT LEAST ONE AT LEAST MONOSUBSTITUTED AMINO GROUP

BACKGROUND OF THE INVENTION

1) Field of the Invention

The invention relates to a method for producing a compound with at least one at least monosubstituted amino group and the use of a compound obtained by such a method.

2) Description of the Related Art

JP 2000-63369 A describes a method for alkylation of melamine in which melamine is reacted with an alcohol at high temperatures in the presence of a metal catalyst on a microporous carrier. Thereby, preferably lower alkylated products are obtained. In this method a low selectivity of the alkylated products on the one hand and the formation of cyanic acid esters as side products by hydrolysis or substitution of the amino groups on the other hand are recognized. The reaction occurs under a nitrogen, argon, hydrogen or carbon monoxide atmosphere.

EP 0 711 760 A1 describes an alkylation of melamine by reacting melamine in the presence of a catalyst and an atmosphere of argon, nitrogen, carbon monoxide or a mixture of hydrogen and carbon monoxide. No complete conversion of the educts and no selectivity in respect to single products are achieved.

EP 1 057 821 A1 describes the alkylation of melamine with alcohols in the presence of catalysts and a nitrogen or hydrogen atmosphere. No complete conversion of the educts and no selectivity in respect to single products are achieved.

Shinoda et al. (Appl. Catalysis A: General 194-195 (2000), 375-381) describes a methylation of melamine starting from methanol. A metal with an acidic carrier is used for the catalysis and the reaction is carried out under protection gas (argon) or hydrogen atmosphere. The reaction achieves a complete conversion, however only after very long reaction times. The formed product spectrum contains different substituted methyl melamines.

SUMMARY OF THE INVENTION

The object of the invention is to provide compounds with at least one monosubstituted amino group, which can be obtained—by introducing multiple substituents in the respective compound—in high selectivity regarding the distribution of the substituents.

DESCRIPTION OF THE PREFERRED EMBODIMENTS

A starting substance having at least one amino group is reacted with an alcohol, whereby the reaction mixture contains liquid or dissolved and/or gaseous ammoniac. The gas phase of the reaction mixture contains in particular gaseous ammoniac. The starting substance and the alcohol are thereby part of a reaction mixture. Ammoniac can also be part of the reaction mixture, for instance in dissolved form. The reaction mixture can be for instance a liquid or dispersion. The amino group of the starting substance has at least one hydrogen atom directly bonded to the nitrogen. This means, that this amino group can be un-substituted or mono-substituted. After conversion with the alcohol R—OH the moiety R is bound to the nitrogen atom of the amino group instead of the original hydrogen atom. With other words, the method according to the invention is a method for derivatizing an amino group.

It has surprisingly been shown that the use of ammonic as gas or as solution in alcohol leads to an almost complete suppression of side products and that the selectivity of the alkylation reaction increases significantly simultaneously. The side product formation by hydrolysis can be in particular significantly reduced or suppressed.

In case of alkylation reactions known from the prior art the presence in particular of air and traces of water leads to the hydrolysis of the formed products, whereby the corresponding alkoxycyanurates are being formed. Such alkoxycyanurates can also be formed, if methanol is substituted by a complete amino group under release of ammoniac. This is not being seen in the method according to the invention.

In order to achieve a possible low side product formation and hydrolysis the molar ratio of ammoniac to alcohol is about 0.1 to about 2, in particular about 0.5 to about 1.5 and specifically in particular about 0.8 to about 1.3. The numbers provided in the present application have always to be understood such that in cases of one-sided open ranges as well closed ranges the upper and the lower limits of the respective range are being included.

In an embodiment the conversion occurs at a total pressure of about 1 to abut 200 bar, in particular at about 40 bar to about 180 bar and specifically in particular at about 60 bar to about 140 bar. The total pressure comprises thereby the ammoniac partial pressure and the partial pressure of further gases contained in the gas phase. Such further gases can be for instance air or nitrogen, whereby smaller amounts of these gases are preferred than larger amounts.

In a variant the conversion occurs under the influence of a catalyst for increasing the conversion rates in order to be able to keep the reaction temperatures on a low level, for increasing the selectivity in respect to the products and/or to reduce the reaction times.

The catalyst comprises in an alternative embodiment a metal or a metal oxide. Also mixtures of different metals and/or metal oxides are possible.

The catalyst is in particular a metal from the $8^{th}$, $9^{th}$ or $10^{th}$ IUPAC-group (VIII. subgroup) of the periodic system. Amongst others iron, cobalt, nickel, ruthenium, rhodium, palladium and platinum belong to said group.

The used amount of a catalyst is in a variant in the area of 0.001 to 20 Mol-%, in particular 0.01 to 10 Mol-%, in particular 0.1 to 1 Mol-% and especially particular 0.1 to 0.5 Mol-% in each case in respect to the amount of the substance of the compound to be converted.

In a further embodiment the catalyst has a carrier material. If for instance a porous carrier material is used the surface of the catalyst can be increased and the amount of the catalytic active metal or metal oxide can be reduced. Suitable carrier materials are for instance zeolithes, alumosilicates, alumophosphates, metal oxides, silicates, layered silicates, aluminium oxide, silicium dioxide and carbon.

Examples for zeolithes are Beta-zeolithe (BEA), Y-zeolithe, faujasite, mordenite, ZSM-5, zeolithe X, zeolithe A.

Examples for layered silicates are montmorillonit, mordenite, bentonite, kaolinite, muskovite, hectorite, fluorhectorite, kanemite, revdite, grumantite, ilerite, saponite, beidelite, nontronite, stevensite, laponite, taneolite, vermiculite, halloysite, volkonskoite, magadite, rectorite, kenyaite, sauconite, borfluorphlogopite and/or synthetic smectites.

The catalysts can be used as powder, molded and monolith catalysts, latter ones for instance on honeycomb structures. For the conversion for instance fixed bad reactors, fluidized bed reactors, steered tank reactors or tubular reactors are used. The reactors are operated in a variant for the conversion under ammoniac atmosphere with pressures of ca. 1 to 200 bar at temperatures up to 280° C. or 300° C. Temperature ranges of ca. 100° C. to ca. 300° C., in particular ca. 150° C. to ca. 250° C. and especially in particular ca. 180° C. to ca. 240° C. are preferred.

The required reaction times are in an embodiment below 20 hours, in particular between ca. 1 Minute and ca. 20 hours, in particular between ca. 1 hour and ca. 10 hours, and especially in particular between ca. 4 hours and ca. 8 hours.

In an alternative embodiment the catalyst is being separated after complete conversion, that means after the reaction has ended or is being interrupted, from the reaction mixture for instance by filtration and is further worked up.

The further work up can be for instance boiling in a solvent at ca. 60° C. to ca. 120° C., in particular ca. 80° C. to ca. 100° C. Through this it is possible to release product bound to the catalyst from the catalyst and thus to increase the yield of the reaction.

In a variant water and/or acetone are used as solvent. A 1:1-mixture (vol/vol) of water and acetone is for instance a suitable solvent.

In a variant the starting substance is a triazine derivative of the general formula (I) or a urea or urea derivative of the general formula (II):

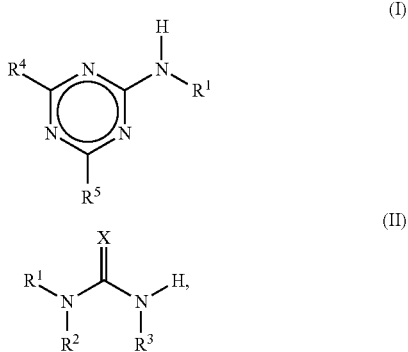

whereby
$R^4$ and $R^5$ mean independently from each other $Q^1$ or a moiety of the formula $R^6$—N—$R^7$ or $R^8$—N—$R^9$ bound with its central nitrogen atom to the triazine ring of the structure of formula (I), whereat
$Q^1$ means a linear or branched $C_1$-$C_{30}$-alkyl or a cyclic substituent in form of a $C_5$-$C_{20}$-cycloalkyl, a $C_5$-$C_{20}$-aryl, a $C_1$-$C_{20}$-alkylsubstituted $C_5$-$C_{20}$-aryl or an amide of a cyclic unsaturated carboxylic acid, whereat the $C_1$-$C_{30}$-alkyl or the cyclic substituent can be interrupted by one or multiple oxygen atoms, sulphur atoms, substituted nitrogen atoms and/or by one or multiple groups of the type —C(O)O—, —OC(O)—, —C(O)— and/or —OC(O)O—,
$R^1$, $R^2$, $R^3$, $R^6$, $R^7$, $R^8$ and $R^9$ mean independently from each other H, linear or branched $C_1$-$C_{20}$-alkyl, $C_5$-$C_{20}$-cyclo alkyl, $C_5$-$C_{20}$-aryl, $C_1$-$C_{20}$-alkylsubstituted $C_5$-$C_{20}$-aryl, which in each case can be interrupted by one or multiple oxygen atoms, sulphur atoms and/or substituted nitrogen atoms and/or by one or multiple groups of the type —C(O)O—, —OC(O)—, —C(O)— and/or —OC(O)O— and/or can be functionalized by one or multiple hydroxyl groups and/or mercapto groups, and
X means O or S.

In a further embodiment a compound having the general formula $R^{10}$—OH is used as an alcohol, whereby
$R^{10}$ means a linear or branched $C_1$-$C_{20}$-alkyl, $C_5$-$C_{20}$-cycloalkyl, or $C_1$-$C_{20}$-alkylsubstituted $C_5$-$C_{20}$-aryl, which can be in each case interrupted by one or multiple oxygen atoms, sulphur atoms, substituted nitrogen atoms and/or by one or multiple groups of the type —C(O)O—, —OC(O)—, —C(O)— and/or —OC(O)O— and/or can be functionalized by one or multiple hydroxyl groups and/or mercapto groups.

In a variant at least one hydroxyl group of the reagent is bound to the alkyl moiety and not to the aryl moiety, if $R^{10}$ means a $C_1$-$C_{20}$-alkylsubstituted $C_5$-$C_{20}$-aryl which can be interrupted or substituted as above. Thereby it can also be provided that all hydroxyl groups are bound to the alkyl moiety and not to the aryl moiety. In this manner the formation of arylated triazine or urea derivatives can be avoided in favour of the formation of arylsubstituted alkylated derivatives.

If hydroxyl groups of the alcohol are present on the alkyl moiety as well as on the aryl moiety in case $R^{10}$ means a $C_1$-$C_{20}$-alkylsubstituted $C_5$-$C_{20}$-aryl, which can as previously be interrupted or substituted, the formation of arylsubstituted alkylated triazine and urea derivatives can still be preferred in respect to arylated derivatives by the selection of suitable reaction conditions. Thus, arylic hydroxyl groups react due to electronic influences of the aromatic general slower than hydroxyl groups bound to an alkyl moiety.

Examples for possible triazine derivatives as starting substances are melamine, benzoguanamine, acetoguanamine, 2,2-dimethylamino-4,6-diamino-1,3,5-triazine, 2,2-dibutylamino-4,6-diamino-1,3,5-triazine, 2,4,6-Tris-(2-hydroxyethyl)amino-1,3,5-triazine, 2-succinimido-4,6-diamino-1,3,5-triazine, and 2,4,6-Tris-methylamino-1,3,5-triazine. Examples for urea derivatives as starting substances are hydroxyethyl urea and ethylene urea. Also non-derivatized urea can be used as starting substance.

A monoalcohol, a polyalcohol (under which also diols and oligoles are to be understood) or a thiol or mixtures thereof are in particular used as alcohols.

Examples for suitable monoalcohols are methanol, ethanol, propanol, isopropanol, butanol, hexanol, decanol, dodecanol, stearylalcohol, glycolmonomethylether, diethylenglycolmonomethylether and bencylalcohol.

Examples for suitable polyalcohohols are ethylenglycol, diethylenglycol, glycerol, trimethylolpropane, pentaerythrit, tripropylenglycol, trisopropanolamine, triethanolamine, hexandiol, butandiol and glycerolmonostearat.

Examples for suitable thiols are mercaptoethanol, mercaptopropanol, mercaptomethylbutanol and mercaptohexanol.

In an embodiment of the method it is sufficient in case of short-chain alcohols as educts for the derivatization of the starting substance to apply the alcohol in excess in order to use said alcohol also as a solvent. In a further variant inert solvents are used as solubilizer when using long-chain alcohols (more than 8, 10 or 12 C-atoms) in order to achieve a better conversion. Basically, solubilizers can also be used with short-chain alcohols if those are for instance highly branched and have therefore a higher viscosity. The application of a solubilizer is always appropriate in such cases when the mixture cannot be stirred anymore without a solubilizer.

Examples for such solubilizers are tetrahydrofurane, diethylether, dimethoxymethane, dimethoxyethane, diethoymethane, diethoxethane, ethylenglycoldiethylether, ethylenglycoldibutylether, diethylenglycoldiethylether, dioxan, benzene, toluene, xylene, mesitylene, cumen, chlorbenzene, pentane, hexane, cyclohexane, heptane, octane, acetonitrile, methylacetate, ethylacetate, menthylbenzoate, N,N-dimethylformamide, N,N-dimethylacetamide, N-methylpyrrolidone, 1,3-dimethylimidazolidinone.

In a variant the produced compound is a triazine derivative of the general formula (III) or a urea derivative of the general formula (IV):

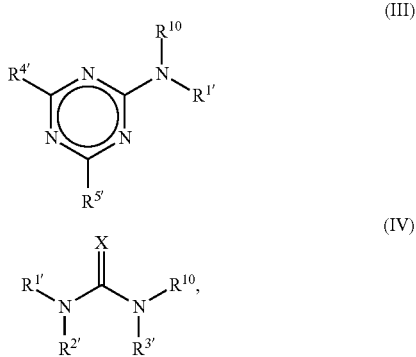

whereby
$R^{4'}$ and $R^{5'}$ mean independently from each other $Q^1$ or a moiety of the formula $R^{6'}$—N—$R^{7'}$— or $R^{8'}$, —N—$R^{9'}$ being bound with its central nitrogen atom to the triazine ring of the structure of the formula (III), whereat
$Q^1$ means a linear or branched $C_1$-$C_{30}$-alkyl or a cyclic substituent in form of a $C_5$-$C_{20}$-cycloalkyl, a $C_5$-$C_{20}$-aryl, a $C_1$-$C_{20}$-alkyl substituted $C_5$-$C_{20}$-aryl or an amide of a cyclic unsaturated carboxylic acid, whereat the $C_1$-$C_{30}$-alkyl or the cyclic substituent can be interrupted by one or multiple oxygen atoms, sulphur atoms, substituted nitrogen atoms and/or by one or multiple groups of the type —C(O)O—, —OC(O)—, —C(O)— and/or —OC(O)O—,
$R^{1'}$, $R^{2'}$, $R^{3'}$, $R^{6'}$, $R^{7'}$, $R^{8'}$ and $R^{9'}$ mean independently from each other,
$R^{10}$,
H
a covalent bond bound to the moiety $R^{10}$ being bound to the same nitrogen atom of the triazine derivative or urea derivative so that a cyclic structure is formed from the nitrogen atom and the moiety $R^{10}$, or
linear or branched $C_1$-$C_{20}$-alkyl, $C_5$-$C_{20}$-cycloalkyl, $C_5$-$C_{20}$-aryl, $C_1$-$C_{20}$-alkyl substituted $C_5$-$C_{20}$-aryl, which in each case can be interrupted by one or multiple oxygen atoms, sulphur atoms and/or substituted nitrogen atoms and/or by one or multiple groups of the type —C(O)O—, —OC(O)—, —C(O)— and/or —OC(O)O— and/or can be functionalized by one or multiple hydroxy groups and/or mercapto groups,
$R^{10}$ means a linear or branched $C_1$-$C_{20}$-alkyl, $C_5$-$C_{20}$-cycloalkyl or $C_1$-$C_{20}$-alkyl substituted $C_5$-$C_{20}$-aryl, which in each case can be interrupted by one or multiple oxygen atoms, sulphur atoms, substituted nitrogen atoms and/or by one or multiple groups of the type —C(O)O—, —OC(O)—, —C(O)— and/or —OC(O)O—, and/or can be functionalized by one or multiple hydroxyl groups and/or mercapto groups, whereby $R^{10}$ can form a cyclic structure with two covalent bonds bonded to the same nitrogen atom of the compounds of the general formula (III) or (IV), whereat one of the two covalent bonds is provided by one of the moieties $R^{1'}$, $R^{2'}$, $R^{3'}$, $R^{6'}$, $R^{7'}$, $R^{8'}$ or $R^{9'}$, X means O or S.

A cyclic structure by the moiety $R^{10}$ is formed for instance if an alcohol is used that carries at least two hydroxyl groups which react in each case with the same nitrogen atom of the starting compound.

In an embodiment of the method at least one moiety, in particular at least two moieties, in particular at least three moieties, in particular at least four moieties, in particular at least five moieties of the moieties $R^{1'}$, $R^{2'}$, $R^{3'}$, $R^{6'}$, $R^{7'}$, $R^{8'}$ and $R^{9'}$ have only the meaning of the moiety $R^{10}$ and in particular not the meaning of H. This is in particular the case if the corresponding moieties $R^{1'}$, $R^{2'}$, $R^{3'}$, $R^{6'}$, $R^{7'}$, $R^{8'}$ and $R^{9'}$ have the meaning of a hydrogen moiety in the starting substance. In other words, several different amino groups of the formed compound (for instance one, two or three amino groups) can be substituted with the moiety $R^{10}$ to a different degree (for instance once or twice) independently from each other.

Applying suitable experimental parameter for instance essentially pure N,N'-dialkyl compounds, N,N',N''-trialkyl compounds or N,N,N',N''-tetraalkyl compounds can be formed. Using suitable experimental parameters also essentially pure N,N'-dihydroxyalkyl compounds, N,N',N''-trihydroxyalkyl compounds, N,N',N''-trihydroxyalkyl-N,N',N''-trialkyl compounds, N,N,N',N''-tetrahydroxyalkyl compounds or N,N,N',N',N'',N''-hexahydroxyalkyl compounds can be synthesized.

In an embodiment the formed compound is selected from the group comprising N-alkymelamin, N,N'-dialkylmelamine, N,N',N''-trialkylmelamine, N,N,N',N''-tetraalkylmelamine, N,N,N',N',N''-pentaalkylmelamine N,N,N',N',N'', N''-hexaalkylmelamine In a further embodiment the formed compound is selected from the group comprising N-alkyl urea, N,N'-dialkylurea, N,N,N'-trialkylurea and N,N,N',N'-tetraalkylurea In a further embodiment the formed compound is selected from the group comprising N-alkylthiolurea, N,N'-dialkylthiolurea, N,N,N'-trialkylthiolurea and N,N, N',N'-tetraalkylthiolurea.

In an alternative embodiment the formed compound is selected from the group comprising N-alkylbenzoguanamine, N,N'-dialkylbenzoguanamine, N,N,N'-trialkylbenzoguanamine and N,N,N',N'-tetraalkylbenzoguanamine In a further alternative embodiment the formed compound is selected from the group comprising N-alkylacetoguanamine, N,N'-dialkyleacetoguanamine and N,N,N'-trialkylacetoguanamine.

In a further embodiment the formed compound is selected from the group comprising N-(hydroxyalkyl)-melamine, N,N'-di-(hydroxyalkyl)-melamine, N,N',N''-tris-(hydroxyalkyl)-melamine, N,N,N',N''-tetra-(hydroxyalkyl)-melamine, N,N,N',N',N''-penta-(hydroxyalkyl)-melamine and N,N,N',N',N'',N''-hexa-(hydroxyalkyl)-melamine.

Thereby in particular methyl, ethyl, butyl and/or hexyl moieties (or their mixtures) are used as alkyl moieties, but also all the other meanings of moiety $R^{10}$ provided above. All moieties $R^{10}$ carrying hydroxyl groups, for instance 2-hydroxyethyl-, hydroxypropyl- and/or hydroxyethoxyethyl moieties can be used as hydroxyalkyl moiety.

By the means of the following reaction equations an exemplary embodiment of the claimed method shall be explained in more detail. Thereby "T" means an increased temperature compared to the room temperature and "p" means an increased pressure in respect to the standard air pressure (specific parameter embodiments or reaction conditions and meanings of the moieties R'' are explained further above):

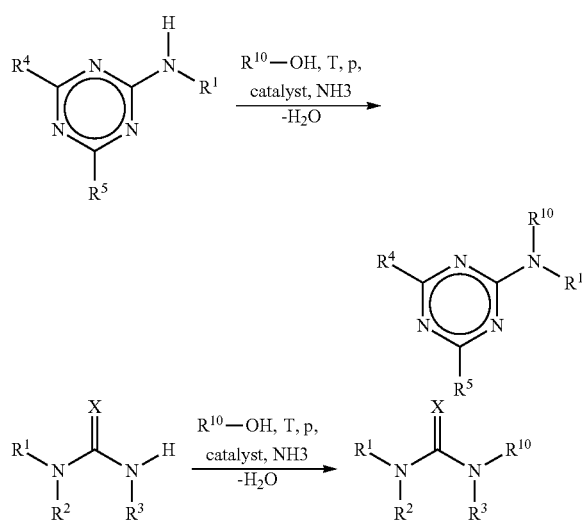

Due to the conversion of the starting substance a hydrogen atom bound to the nitrogen of an amino group is replaced by the moiety $R^{10}$ of the used alcohol; a derivatization of the amino group occurs. After completion of the reaction the derivatized amino group has at least one substituent being different from a hydrogen atom, namely $R^{10}$. Depending on the reaction conditions also further moieties $R^n$, which previously had the meaning of a hydrogen atom, can be replaced by the moiety $R^{10}$. In this manner compounds with different degrees of substituted amino groups can be obtained.

Due to the obtained purity the derivatized, in particular alkylated, compounds obtained according to this method as for instance alkylated amino triazines and alkylated ureas can be used as formaldehyde resins. Under the meaning "formaldehyde resin" a resin made of formaldehyde and the corresponding formed compound is to be understood. These formaldehyde resins have specific properties in respect to rheology, hydrophilicity or lipophilicity and surface properties. They are in particular suitable for application in the area of the laminate coating of the wood processing industry.

In particular alkylated compounds as for instance the symmetrical trialkyl melamine (N,N',N''-trialkyl melamine) are also suitable as cross linker. Further areas of use of the formed compounds, in particular of the alkylated compounds as for instance the alkylated aminotriazines and the alkylated ureas are the area of additives for plasticization, the area of flame retardant additives, the area of comonomers for a polyurethane and the area of agrochemicals.

Since due to an alkylation (in particular if longer-chained alkyl moieties are bound to the starting substance having an amino group) the hydrophobicity of the formed compound is increased compared to the starting substance, the compounds obtained by the claimed method can be used in a mixture with a polyolefine, in particular a polyethylene (polyethen) or polypropylene (polypropen). In this manner the flame retardant properties or surface properties of an object made of a mixture of the polyolefin and the formed compound can be for instance improved compared to the corresponding properties of an object made if an unmodified polyolefin.

Further details of the invention are explained in more detail by the means of the following examples, whereby the first comparative example 1 reflects a method according to the prior art with lower selectivity in respect to the formed compounds. If there is nothing different stated explicitly, all percent numbers in the examples as well as in the remaining parts of the description and the claims are to be understood as mass percentage.

Synthesis of N,N'-dimethylmelamine

COMPARATIVE EXAMPLE 1

In a 500 ml stirring autoclave 5.0 g melamine, 104 g methanol and 10.1 g of a Ni/Y-zeolithe catalyst are intensively mixed, so that the catalyst does not sink to the bottom. After closing the autoclave it is being heated to 200° C. Thereby, a pressure of 40 bar is set up. After 6 hours reaction time the reaction is aborted and the autoclave is cooled and depressurizd. The cooled solution is separated from the catalyst via a filter. The catalyst is boiled with acetone/water-mixture (1:1) at 80° C. The filtrate and the washing solution were united and concentrated up to dryness. The obtained product is dried in the vacuum drying cabinet at 40° C. In this manner 4.9 g product were isolated what corresponds to a yield of 81% in respect to the used melamine. A determination of the composition of the product by the means of quantitative HPLC yielded 25.7% melamine, 10.1% N-methyl melamine, 1.2% N,N-dimethyl melamine, 1.6% N,N'-dimethyl melamine, 8.5% O-methylammelin, 9.3% 0,0'-dimethylamelid and 43.6% trimethylcyanurate.

EXAMPLE 1a

In a 500 ml stirring autoclave 5.0 g melamine, 205 g methanol and 10.2 g of a Ni/Y-zeolithe catalyst are intensively mixed, so that the catalyst does not sink to the bottom. After closing the autoclave 105 g ammoniac are pressed into the reactor and is being heated up to 210° C. Thereby, a pressure of 130 bar is set up. After 3 hours reaction time the reaction is aborted and the autoclave is cooled and depressurized. The cooled solution is separated from the catalyst via a filter. The catalyst is boiled with an acetone/water-mixture (1:1) at 80° C. The filtrate and the washing solution were united and concentrated up to dryness. The obtained product is dried in the vacuum drying cabinet at 40° C. In this manner 4.7 g product were isolated. A determination of the composition of the product by the means of quantitative HPLC yielded 93.6% N,N'-dimethyl melamine, 5.0% N-methyl melamine and 1.3% N,N',N''-trimethyl melamine and 0.1% trimethylcyanurate.

EXAMPLE 1b

In a 500 ml stirring autoclave 5.4 g melamine, 109 g methanol and 10.3 g of a Ru/Mordenit catalyst are intensively mixed, so that the catalyst does not sink to the bottom. After closing the autoclave 105 g ammoniac are pressed into the reactor and heated up to 200° C. Thereby, a pressure of 120 bar is set up. After 6 hours reaction time the reaction is aborted and the autoclave is cooled and depressurized. The cooled solution is separated from the catalyst via a filter. The catalyst is boiled with an acetone/water-mixture (1:1) at 80° C. The filtrate and the washing solution were united and concentrated up to dryness. The obtained product is dried in the vacuum drying cabinet at 40° C. In this manner 6.6 g product were isolated. A determination of the composition of the product by the means of quantitative HPLC yielded 62% N,N'-dimethyl melamine, 2.1% N-methylmelamine and 35.9% N,N',N''-trimethylmelamine.

Synthesis of N,N',N''-Trimethylmelamine

EXAMPLE 2a

In a 500 ml stirring autoclave 5.3 g melamine, 107 g methanol and 10.4 g of a Ru/BEA catalyst are intensively mixed, so that the catalyst does not sink to the bottom. After closing the autoclave 100 g ammoniac are pressed into the reactor and heated to 230° C. Thereby, a pressure of 140 bar is set up. After 4 hours reaction time the reaction is aborted and the autoclave is cooled and depressurized. The cooled solution is separated from the catalyst via a filter. The catalyst is boiled with an acetone/water-mixture (1:1) at 80° C. The filtrate and the washing solution were united and concentrated up to dryness. The obtained product is dried in the vacuum drying cabinet at 40° C. In this manner 6.5 g product were isolated. A determination of the composition of the product by the means of quantitative HPLC yielded 99% N,N',N"-trimethyl melamine and 1% N,N,N',N"-tetramethyl melamine.

EXAMPLE 2b

In a 500 ml stirring autoclave 5.3 g melamine, 120 g of a 50% ammoniac containing methanol solution and 10.4 g of a Ru/BEA catalyst are intensively mixed, so that the catalyst does not sink to the bottom. After closing the autoclave is heated to 230° C. Thereby, a pressure of 70 bar is set up. After 4 hours reaction time the reaction is aborted and the autoclave is cooled and depressurized. The cooled solution is separated from the catalyst via a filter. The catalyst is boiled with an acetone/water-mixture (1:1) at 80° C. The filtrate and the washing solution were united and concentrated up to dryness. The obtained product is dried in the vacuum drying cabinet at 40° C. In this manner 6.7 g product were isolated. A determination of the composition of the product by the means of quantitative HPLC yielded 97.6% N,N',N"-trimethyl melamine and 2.4% N,N,N',N"-tetramethyl melamine.

Synthesis of N,N,N',N"-Tetramethylmelamine

EXAMPLE 3a

In a 500 ml stirring autoclave 5.4 g melamine, 208 g methanol and 10.3 g of a Ru/BEA catalyst are intensively mixed, so that the catalyst does not sink to the bottom. After closing the autoclave 55.5 g ammoniac are pressed into the reactor and heated to 230° C. Thereby, a pressure of 140 bar is set up. After 8 hours reaction time the reaction is aborted and the autoclave is cooled and depressurized. The cooled solution is separated from the catalyst via a filter. The catalyst is boiled with an acetone/water-mixture (1:1) at 80° C. The filtrate and the washing solution were united and concentrated up to dryness. The obtained product is dried in the vacuum drying cabinet at 40° C. In this manner 6.9 g product were isolated. A determination of the composition of the product by the means of quantitative HPLC yielded 72.3% N,N,N',N"-tetramethylmelamine, 25.8% N,N',N"-trimethylmelamine and 1.1% N,N,N'-trimethylmelamine and 0.8% N,N,N',N'-tetramethylmelamine.

EXAMPLE 3b

In a 500 ml stirring autoclave 5.1 g of a mixture of 30% N-methyl melamine, 34% N,N'-dimethyl melamine and 36% N,N',N"-trimethyl melamine, 202 g methanol and 10.4 g of a Ru/BEA catalyst are intensively mixed, so that the catalyst does not sink to the bottom. After closing the autoclave 60 g ammoniac are pressed into the reactor and heated to 240° C. Thereby, a pressure of 135 bar is set up. After 4 hours reaction time the reaction is aborted and the autoclave is cooled and depressurized. The cooled solution is separated from the catalyst via a filter. The catalyst is boiled with an acetone/water-mixture (1:1) at 80° C. The filtrate and the washing solution were united and concentrated up to dryness. The obtained product is dried in the vacuum drying cabinet at 40° C. In this manner 5.4 g product were isolated. A determination of the composition of the product by the means of quantitative HPLC yielded 84.2% N,N,N',N"-tetramethylmelamine, 15.6% N,N',N"-trimethylmelamine and 0.2% N,N,N',N',N"-pentamethylmelamine.

Synthesis of N,N',N"-Triethylmelamine

EXAMPLE 4

In a 500 ml stirring autoclave 5.1 g melamine, 303 g ethanol and 10.2 g of a Ni/NiO catalyst are intensively mixed, so that the catalyst does not sink to the bottom. After closing the autoclave 103.8 g ammoniac are pressed into the reactor and heated to 240° C. Thereby, a pressure of 155 bar is set up. After 4 hours reaction time the reaction is aborted and the autoclave is cooled and depressurized. The cooled solution is separated from the catalyst via a filter. The catalyst is boiled with an acetone/water-mixture (1:1) at 80° C. The filtrate and the washing solution were united and concentrated up to dryness. The obtained product is dried in the vacuum drying cabinet at 40° C. In this manner 7.8 g product were isolated. A determination of the composition of the product by the means of quantitative HPLC yielded 94.6% N,N',N"-triethylmelamine and 5.4% N,N,N',N"-tetraethylmelamine.

Methylation of Urea

EXAMPLE 5

In a 500 ml stirring autoclave 3.0 g urea, 80 g methanol and 5 g of a Ru/BEA catalyst are intensively mixed, so that the catalyst does not sink to the bottom. After closing the autoclave 100 g ammoniac are pressed into the reactor and heated to 200° C. After 4 hours reaction time the reaction is aborted and the autoclave is cooled and depressurized. The cooled solution is separated from the catalyst via a filter. The catalyst is boiled with an acetone/water-mixture (1:1) at 80° C. The filtrate and the washing solution were united and concentrated up to dryness. The obtained product is dried in the vacuum drying cabinet at 40° C. In this manner 3.5 g product were isolated. A determination of the composition of the product by the means of quantitative HPLC yielded 84.6% N,N'-dimethylurea, 3.4% N-monomethylurea and 12% N,N,N'-trimethyl urea.

Methylation of Benzoguanamine

EXAMPLE 6

In a 500 ml stirring autoclave 6.0 g benzoguanamine, 110 g methanol and 9.5 g of a Ni/NiO catalyst are intensively mixed, so that the catalyst does not sink to the bottom. After closing the autoclave 80 g ammoniac are pressed into the reactor and heated to 240° C. After 4 hours reaction time the reaction is aborted and the autoclave is cooled and depressurized. The cooled solution is separated from the catalyst via a filter. The catalyst is boiled with acetone. The filtrate and the washing solution were united and concentrated up to dryness. The obtained product is dried in the vacuum drying cabinet at 40° C. In this manner 6.5 g product were isolated. A determination of the composition of the product by the means of quantitative HPLC yielded 78.5% N,N'-dimethyl benzoguanamine, 6.7% N-monomethylbenzoguanamine and 14.8% N,N,N'-trimethylbenzoguanamine.

Ethylation of Acetoguanamine

EXAMPLE 7

In a 500 ml stirring autoclave 5.6 g acetoguanamine, 290 g ethanol and 10.2 g of a Ru/TiO$_2$ catalyst are intensively mixed, so that the catalyst does not sink to the bottom. After closing the autoclave 100 g ammoniac are pressed into the reactor and heated to 210° C. After 3 hours reaction time the reaction is aborted and the autoclave is cooled and depressurized. The cooled solution is separated from the catalyst via a filter. The catalyst is boiled with an acetone/water-mixture (1:1) at 80° C. The filtrate and the washing solution were united and concentrated up to dryness. The obtained product is dried in the vacuum drying cabinet at 40° C. In this manner 6.5 g product were isolated. A determination of the composition of the product by the means of quantitative HPLC yielded 74.8% N,N'-diethylacetoguanamine and 25.2% N,N,N'-triethylacetoguanamine.

Synthesis of Hexylmelamine

EXAMPLE 8

In a 1000 ml stirring autoclave 5.1 g melamine, 500 g hexanol and 10.2 g of a Ni/NiO catalyst are intensively mixed, so that the catalyst does not sink to the bottom. After closing the autoclave 103.8 g ammoniac are pressed into the reactor and heated to 250° C. After 8 hours reaction time the reaction is aborted and the autoclave is cooled and depressurized. The obtained solution is separated from the catalyst via a filter. The catalyst is boiled with acetone at 80° C. The filtrate and the washing solution were united and concentrated up to dryness. The obtained product is dried in the vacuum drying cabinet at 40° C. In this manner 7.8 g product were isolated. A determination of the composition of the product by the means of quantitative HPLC yielded 55% N,N',N''-trihexylmelamine, 27% N,N'-dihexylmelamine and 15% N-monohexylmelamine and 3% melamine.

Synthesis of Tris-(2-hydroxyethyl)-Melamine

EXAMPLE 9

In a 1000 ml stirring autoclave 5.0 g melamine, 400 g ethylene glycol and 9.5 g of a Ru/Mordenit catalyst are intensively mixed, so that the catalyst does not sink to the bottom. After closing the autoclave 120 g ammoniac are pressed into the reactor and heated to 210° C. After 6 hours reaction time the reaction is aborted and the autoclave is cooled and depressurized. The cooled solution is separated from the catalyst via a filter. The catalyst is boiled with water at 100° C. The filtrate and the washing solution were united and concentrated up to dryness. The obtained product is dried in the vacuum drying cabinet at 40° C. In this manner 8.1 g product were isolated. A determination of the composition of the product by the means of quantitative HPLC yielded 64% N,N',N''-tris-(2-hydroxyethyl) melamine, 16% N,N'-di-(2-hydroxyethyl) melamine and 6% N-mono-(2-hydroxyethyl) melamine and 14% N,N,N',N''-tetra-(2-hydroxyethyl) melamine.

Synthesis of N,N',N''-Tris-(2-hydroxyethyl)-N,N',N''-Trimethylmelamine

EXAMPLE 10

In a 1000 ml stirring autoclave 5.5 g N,N',N''-tris-(2-hydroxyethyl)-melamine, 250 g methanol and 10.2 g of a Ru/Al$_2$O$_3$ catalyst are intensively mixed, so that the catalyst does not sink to the bottom. After closing the autoclave 160 g ammoniac are pressed into the reactor and heated to 200° C. After 6 hours reaction time the reaction is aborted and the autoclave is cooled and depressurized. The cooled solution is separated from the catalyst via a filter. The catalyst is boiled with an acetone/water-mixture (1:1) at 80° C. The filtrate and the washing solution were united and concentrated up to dryness. The obtained product is dried in the vacuum drying cabinet at 40° C. In this manner 5.9 g product were isolated. A determination of the composition of the product by the means of quantitative HPLC yielded 85% N,N',N''-tris-(2-hydroxyethyl)-N,N',N''-trimethylmelamine, 12% N,N',N''-tris-(2-hydroxyethyl)-N,N'-dimethylmelamine and 3% N,N',N''-tris-(2-hydroxyethyl)-N-monomethylmelamine.

Synthesis of Hexa-(2-hydroxyethyl)-melamine

EXAMPLE 11

In a 1000 ml stirring autoclave 5.0 g melamine, 250 g ethylene glycol and 10.5 g of a Ru/BEA catalyst are intensively mixed, so that the catalyst does not sink to the bottom. After closing the autoclave 120 g ammoniac are pressed into the reactor and heated to 200° C. After 14 hours reaction time the reaction is aborted and the autoclave is cooled and depressurized. The cooled solution is separated from the catalyst via a filter. The catalyst is boiled with water at 100° C. The filtrate and the washing solution are united and concentrated up to dryness. The obtained product is re-crystallized from butanol and dried in the vacuum drying cabinet at 40° C. In this manner 11.3 g product were isolated. A determination of the composition of the product by the means of quantitative HPLC yielded 53% N,N,N',N',N'',N''-hexa-(2-hydroxyethyl)-melamine, 18% N,N,N',N',N''-penta-(2-hydroxyethyl)-melamine, 16% N,N,N',N''-tetra-(2-hydroxethyl)-melamine, 9% N,N',N''-tris-(2-hydroxyethyl)-melamine and 4% N,N'-di-(2-hydroxyethyl)-melamine

The invention claimed is:
1. A method for producing at least one compound having at least one at least monosubstituted amino group, comprising a starting substance having at least one amino group in form of a triazine derivative of the general formula (I) or a urea or urea derivative of the general formula (II):

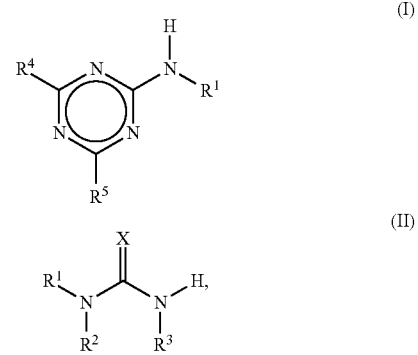

whereby
$R^4$ and $R^5$ mean independently from each other $Q^1$ or a moiety of the formula $R^6$—N—$R^7$ or $R^8$—N—$R^9$ bound with its central nitrogen atom to the triazine ring of the structure of formula (I), whereas
$Q^1$ means a linear or branched $C_1$-$C_{30}$-alkyl or a cyclic substituent in form of a $C_5$-$C_{20}$-cycloalkyl, a $C_5$-$C_{20}$-aryl, a $C_1$-$C_{20}$-alkylsubstituted $C_5$-$C_{20}$-aryl or an amide of a cyclic unsaturated carboxylic acid, whereat the $C_1$-$C_{30}$-alkyl or the cyclic substituent can be interrupted by one or multiple oxygen atoms, sulphur atoms, substituted nitrogen atoms and/or by one or multiple groups of the type —C(O)O—, —OC(O)—, —C(O)— and/or —OC(O)O—, $R^1$, $R^2$, $R^3$, $R^6$, $R^7$, $R^8$ and $R^9$ mean independently from each other H, linear or branched $C_1$-$C_{20}$-alkyl, $C_5$-$C_{20}$-cyclo alkyl, $C_5$-$C_{20}$-aryl, $C_1$-$C_{20}$-alkylsubstituted $C_5$-$C_{20}$-aryl, which in each case can be interrupted by one or multiple oxygen atoms, sulphur atoms and/or substituted nitrogen atoms and/or by one or multiple groups of the type —C(O)O—, —OC(O)—, —C(O)— and/or —OC(O)O— and/or can be functionalized by one or multiple hydroxyl groups and/or mercapto groups, and X means O or S, is reacted with an alcohol of the general formula $R^{10}$—OH, whereby $R^{10}$ means a linear or branched $C_1$-$C_{20}$-alkyl, $C_5$-$C_{20}$-cycloalkyl, or $C_1$-$C_{20}$-alkylsubstituted $C_5$-$C_{20}$-aryl, which can be in each case interrupted by one or multiple oxygen atoms, sulphur atoms, substituted nitrogen atoms and/or by one or multiple groups of the type —C(O)O—, —OC(O)—, —C(O)— and/or —OC(O)O— and/or can be functionalized by one or multiple hydroxyl groups and/or mercapto groups, in a reaction mixture in the presence of ammonia, whereby the molar ratio of ammonia to alcohol is 0.1 to 2.

2. The method according to claim 1, wherein the conversion occurs at a total pressure of 1 to 200 bar.

3. The method according to claim 1, wherein the reaction mixture contains a catalyst.

4. The method according to claim 3, wherein the catalyst has a metal or a metal oxide or both.

5. The method according to claim 4, wherein the metal or the metal oxide or both comprises a metal from the $8^{th}$, $9^{th}$ or $10^{th}$ group of the periodic system.

6. The method according to claim 3, wherein the catalyst has a carrier material.

7. The method according to claim 6, wherein the carrier material is a zeolithe, an alumo silicate, an alumo phosphate, a metal oxide, a silicate, a layered silicate, an aluminium oxide, silicon dioxide, or carbon.

8. The method according to claim 3, wherein the catalyst is separated after the completed reaction from the reaction mixture and is further processed.

9. The method according to claim 8, wherein the catalyst is heated during the further processing at 60° C. to 120° C. in a solvent.

10. The method according to claim 9, wherein the solvent comprises water or acetone or both.

11. The method according to claim 1, wherein the conversion occurs at a temperature of 100° C. to 300° C.

12. The method according to claim 1, wherein the conversion occurs during a reaction time of 1 minute to 20 hours.

13. The method according to claim 1, wherein at least one hydroxyl group of the alcohol is present on the alkyl moiety and not on the aryl moiety if $R^{10}$ means a $C_1$-$C_{20}$-alkyl substituted $C_5$-$C_{20}$-aryl.

14. The method according to claim 1, wherein the alcohol is a monoalcohol, a polyalcohol or a thiol.

15. The method according to claim 1, wherein the produced compound is a triazine derivative of the general formula (III) or a urea derivative of the general formula (IV):

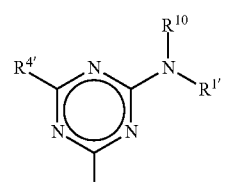

(III)

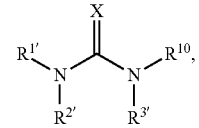

(IV)

whereby $R^{4'}$ and $R^{5'}$ mean independently from each other $Q^1$ or a moiety of the formula $R^{6'}$—N—$R^{7'}$— or $R^{8'}$—N—$R^{9'}$ being bound with its central nitrogen atom to the triazine ring of the structure of the formula (III), whereas $Q^1$ means a linear or branched $C_1$-$C_{30}$-alkyl or a cyclic substituent in form of a $C_5$-$C_{20}$-cycloalkyl, a $C_5$-$C_{20}$-aryl, a $C_1$-$C_{20}$-alkyl substituted $C_5$-$C_{20}$-aryl or an amide of a cyclic unsaturated carboxylic acid, whereas the $C_1$-$C_{30}$-alkyl or the cyclic substituent can be interrupted by one or multiple oxygen atoms, sulphur atoms, substituted nitrogen atoms and/or by one or multiple groups of the type —C(O)O—, —OC(O)—, —C(O)— and/or —OC(O)O—, $R^{1'}$, $R^{2'}$, $R^{3'}$, $R^{6'}$, $R^{7'}$, $R^{8'}$ and $R^{9'}$ mean independently from each other, $R^{10}$,

H, a covalent bond bound to the moiety $R^{10}$ being bound to the same nitrogen atom of the triazine derivative or urea derivative so that a cyclic structure is formed from the nitrogen atom and the moiety $R^{10}$, or linear or branched $C_1$-$C_{20}$-alkyl, $C_5$-$C_{20}$-cycloalkyl, $C_5$-$C_{20}$-aryl, $C_1$-$C_{20}$-alkyl substituted $C_5$-$C_{20}$-aryl, which in each case can be interrupted by one or multiple oxygen atoms, sulphur atoms and/or substituted nitrogen atoms and/or by one or multiple groups of the type —C(O)O—, —OC(O)—, —C(O)— and/or —OC(O)O— and/or can be functionalized by one or multiple hydroxy groups and/or mercapto groups, $R^{10}$ means a linear or branched $C_1$-$C_{20}$-alkyl, $C_5$-$C_{20}$-cycloalkyl or $C_1$-$C_{20}$-alkyl substituted $C_5$-$C_{20}$-aryl, which in each case can be interrupted by one or multiple oxygen atoms, sulphur atoms, substituted nitrogen atoms and/or by one or multiple groups of the type —C(O)O—, —OC(O)—, —C(O)— and/or —OC(O)O—, and/or can be functionalized by one or multiple hydroxyl groups and/or mercapto groups, whereby $R^{10}$ can form a cyclic structure with two covalent bonds bonded to the same nitrogen atom of the compounds of the general formula (III) or (IV), whereat one of the two covalent bonds is provided by one of the moieties $R^{1'}$, $R^{2'}$, $R^{3'}$, $R^{6'}$, $R^{7'}$, $R^{8'}$ or $R^{9'}$, X means O or S.

16. The method according to claim 15, wherein the at least one moiety of the moieties $R^{1'}$, $R^{2'}$, $R^{3'}$, $R^{6'}$, $R^{7'}$, $R^{8'}$ and $R^{9'}$ have the meaning of the moiety $R^{10}$.

17. The method according to claim 1, wherein the formed compound is selected from the group consisting of N,N'-dialkyl melamine, N,N',N''-trialkyl melamine, and N,N,N',N''-tetraalkyl melamine.

18. The method according to claim 1, wherein the foamed compound is selected from the group consisting of N-mono alkyl urea, N,N'-dialkyl urea, and N,N,N'-trialkyl urea.

19. The method according to claim 1, wherein the formed compound is selected from the group consisting of N-monoalkylthiolurea, N,N'-dialkylthiolurea, and N,N,N'-trialkylthiolurea.

20. The method according to claim 1, wherein the formed compound is selected from the group consisting of N,N'-dialkylbenzoguanamine, N,N,N'-trialkylbenzoguanamine, N,N'-dialkyleacetoguanamine, and N,N,N'-trialkylacetoguanamine.

21. The method according to claim 1, wherein the formed compound is selected from the group consisting of N,N'-di-(hydroxyalkyl)-melamine, N,N',N"-tris-(hydroxyalkyle)-melamine, N,N,N',N"-tetra-(hydroxyalkyl)-melamine, N,N,N',N',N"-penta-(hydroxyalkyl)-melamine, and N,N,N',N',N",N"-hexa-(hydroxyalkyl)-melamine.

22. A method of producing oligomers, polymers, or a formaldehyde resin, comprising a step of producing a compound according to claim 1.

23. The method according to claim 22, wherein the formaldehyde resin is used as a laminate coating.

24. A method of producing a polyolefin containing mixture, comprising the steps of producing a compound according to claim 1 and mixing the compound with a polyolefin.

* * * * *